US010925475B2

(12) United States Patent
Horvitz (10) Patent No.: US 10,925,475 B2
(45) Date of Patent: Feb. 23, 2021

(54) SYSTEM, DEVICE AND METHOD FOR ADVANCING AN ARTICLE ALONG A PATH

(71) Applicant: CONSIS MEDICAL LTD., Beer-Sheva (IL)

(72) Inventor: Amir Horvitz, Moshav Nir Akiva (IL)

(73) Assignee: CONSIS MEDICAL LTD., Beer Sheva (IL)

( * ) Notice: Subject to any disclaimer, the term of this patent is extended or adjusted under 35 U.S.C. 154(b) by 887 days.

(21) Appl. No.: 15/529,311

(22) PCT Filed: Nov. 22, 2015

(86) PCT No.: PCT/IL2015/051121
§ 371 (c)(1),
(2) Date: May 24, 2017

(87) PCT Pub. No.: WO2016/084064
PCT Pub. Date: Jun. 2, 2016

(65) Prior Publication Data
US 2017/0258306 A1 Sep. 14, 2017

Related U.S. Application Data (60) Provisional application No. 62/083,688, filed on Nov. 24, 2014.

(51) Int. Cl.
| | | |
|---|---|---|
| A61B 1/05 | (2006.01) |
| A61B 1/00 | (2006.01) |
| A61B 1/01 | (2006.01) |
| A61M 25/01 | (2006.01) |
| A61B 1/018 | (2006.01) |
| B29L 23/00 | (2006.01) |

(52) U.S. Cl.
CPC ............ *A61B 1/05* (2013.01); *A61B 1/00135* (2013.01); *A61B 1/00151* (2013.01); *A61B 1/01* (2013.01); *A61M 25/01* (2013.01); *A61M 25/0122* (2013.01); *A61B 1/00002* (2013.01); *A61B 1/00016* (2013.01); *A61B 1/00071* (2013.01); *A61B 1/018* (2013.01); *A61M 25/0119* (2013.01); *B29L 2023/00* (2013.01)

(58) Field of Classification Search
CPC .......... A61M 25/0119; A61M 25/0113; A61M 35/01; A61M 25/0122; B29L 2023/00; A61B 1/05; A61B 1/00135; A61B 1/00151; A61B 1/01; A61B 1/00002; A61B 1/00016; A61B 1/00071; A61B 1/018

See application file for complete search history.

(56) References Cited

U.S. PATENT DOCUMENTS

| | | |
|---|---|---|
| 4,043,345 A | 8/1977 | Kramann et al. |
| 4,077,610 A | 3/1978 | Masuda |
| 4,493,711 A | 1/1985 | Chin et al. |

(Continued)

FOREIGN PATENT DOCUMENTS

| | | |
|---|---|---|
| CN | 1293550 A | 5/2001 |
| CN | 102905608 A | 1/2013 |

(Continued)

*Primary Examiner* — Patrick Fernandes
(74) *Attorney, Agent, or Firm* — Vorys, Sater, Seymour and Pease LLP; William L. Klima (57) ABSTRACT

Provided is a system for advancing an article along a path. The system may include a head member, a dispatching member, and an eversion sleeve. Also provided is a method for assembling a system for advancing an article along a path.

20 Claims, 10 Drawing Sheets

(56) References Cited

U.S. PATENT DOCUMENTS

| | | | |
|---|---|---|---|
| 5,259,364 A | 11/1993 | Bob et al. | |
| 2001/0044595 A1 | 11/2001 | Reydel et al. | |
| 2003/0105386 A1 | 6/2003 | Voloshin et al. | |
| 2003/0168068 A1 | 9/2003 | Poole et al. | |
| 2003/0208223 A1 | 11/2003 | Kleiner | |
| 2007/0203472 A1 | 8/2007 | Nachmani | |
| 2011/0009943 A1 | 1/2011 | Paul et al. | |
| 2011/0139665 A1 | 6/2011 | Madsen | |
| 2013/0035749 A1 | 2/2013 | Farag | |

FOREIGN PATENT DOCUMENTS

| | | |
|---|---|---|
| JP | 2004-508084 A | 3/2004 |
| WO | 2010/020985 A1 | 2/2010 |

# SYSTEM, DEVICE AND METHOD FOR ADVANCING AN ARTICLE ALONG A PATH

TECHNICAL FIELD

This presently disclosed subject matter relates to the field of systems and methods for advancing an article along a path.

BACKGROUND

The principle of an eversion sleeve to be used in conjunction with a catheter is known for many years in the field of medical devices. Such sleeves are used for enabling an access to different body cavities such as the colon system or the urethral system, and navigating within respective biological lumens. Below are a number of prior art examples in which a device having an eversion sleeve is used.

U.S. Pat. No. 4,493,711 discloses a catheter having an inverted-evertable non-elastic tube with a diameter throughout equal to or greater than the catheter body, an axially aligned end opening at the distal end, and a multifold configuration of the distal end to maintain end-sealing during inversion and eversion.

US 2003/208223 discloses an apparatus incorporating an elongate hollow element for being positioned along a body cavity of a patient. The hollow element has a leading region and a trailing region and is arranged for being progressively everted along the hollow element from the leading region to thereby be increasingly extended for progressively lining the body cavity as the trailing region follows along.

U.S. Pat. No. 4,043,345 discloses a catheter including a flexible hose attached to one end of a rigid tube through which fluid pressure may be applied to invert said hose from an invaginated position within said tube to an exserted position extending outwardly of said tube having formed at the distal of said hose a valve which remains closed when the hose is in the invaginated position and which opens with the hose in its exserted position.

SUMMARY OF THE PRESENTLY DISCLOSED SUBJECT MATTER

According to one aspect of the presently disclosed subject matter, there is provided a system for advancing an article along a path, comprising:
  a head member;
  a dispatching member; and
  an eversion sleeve configured with an outside portion having a sleeve end configured to be fixed to the dispatching member, an everting portion configured for slidingly articulating to the head member and an inside portion configured to extend from the everting portion towards the dispatching member;
  said inside portion and said outside portion are configured to form a space therebetween for receiving a propelling fluid for exerting force on the everting portion, thereby gradually advancing a segment of the inside portion towards the head member causing it to slidingly displace with respect to the head member and gradually advancing a respective segment of the everting portion into the outside portion, thereby everting said eversion sleeve inside out and advancing the head member along the path;
  wherein said head member is configured with an internal portion for retaining the everting portion and facilitating the everting portion to slide with respect to the head member.

According to a further aspect of the presently disclosed subject matter, there is provided a device for advancing an article along a path, comprising:
  a head member;
  a dispatching member;
  an eversion sleeve configured with an outside portion having a sleeve end fixed to the dispatching member, an everting portion slidingly articulated to the head member and an inside portion extending from the everting portion towards the dispatching member; and
  a space formed between said inside portion and said outside portion for receiving a propelling fluid for exerting force on the everting portion, thereby gradually advancing a segment of the inside portion towards the head member causing it to slidingly displace with respect to the head member and gradually advancing a respective segment of the everting portion into the outside portion, thereby everting said eversion sleeve inside out and advancing the head member along the path;
  wherein said head member is configured with an internal portion for retaining the everting portion and facilitating the everting portion to slide with respect to the head member.

The term 'article' as used herein in the specification and claims, denotes the head member with or without an electric or mechanical unit mounted thereto, a video camera, a stills camera, an imaging system, sensing system, a treatment system, a working tool, a communication system, a treatment equipment, etc.

The term 'path' as used herein in the specification and claims, denotes a canal, a channel, a cavity, a tunnel, an underpass, a lumenway, a tube, a lumen, a conduit, etc.

The term 'fluid' as used herein in the specification and claims, denotes a gaseous fluid, such as air, helium, etc. or a liquid fluid such as water, oil, etc.

The eversion sleeve of the presently disclosed subject matter is made of a resilient and/or flexible material that allows advancing the eversion sleeve with the head member mounted thereto along a curved path with the ability to curve and bend the eversion sleeve during the advancement when contacting the walls of the path, thereby following the path. During advancement of the eversion sleeve, it will follow a path of least resistance, so when a bend occurs, the eversion sleeve will follow it.

The eversion process involves deployment of the eversion sleeve by turning it inside out. This allows advancing the eversion sleeve and its head member with a substantially low friction within the internal surface of the path that can be rough and can include various obstacles therealong, thereby allowing easy and reliable self-propulsion of the head member along the path. Eventually, the eversion process is such that the outside portion of the sleeve remains substantially stationary with respect to the walls of the path, and the main element that may be subject to friction with the path is the head member.

Any one or more of the following features, designs and configurations can be incorporated in the system and the device of presently disclosed subject matter, independently or in combination thereof:

The head member can be made of a substantially rigid material that preserves its shape also when the force exerted by the propelling fluid on the everting portion is reduced or terminated (i.e., the pressure of the propelling fluid within the space drops). This can allow the head member and/or the entire device to perform its designated function at any location along the path also when there is a pressure drop of propelling fluid.

The everting portion can be configured with an external surface engaging the internal portion of the head member, and an internal surface on which the force of the propelling fluid is to be exerted.

The internal portion of the head member can be configured with at least one narrow portion having a first cross-sectional diameter D1 taken perpendicularly to its length and at least one wide portion having a second cross-sectional diameter D2 taken perpendicularly to its length, which is greater than D1. The at least one narrow portion is configured to engage the external surface of the everting portion and prevent axial displacement of the head member with respect to the everting portion, while allowing the everting portion to slidingly displace with respect to the internal portion.

The narrow portion can be formed as a circumferential groove formed in the head member.

The at least one narrow portion can be disposed closer to the outside portion than the at least one wide portion.

The at least one narrow portion can be disposed between two of said wide portions.

The head member can further comprise a retaining member configured for engaging the internal surface of the everting portion and applying an outwardly pressing force thereon, thereby retaining the everting portion in proximity to the internal portion while allowing the everting portion for slidingly displacing with respect to the internal portion.

The retaining member can be located in close proximity to the wide portion of the internal portion. The retaining member can have an exterior face having a shape which is mimicking the shape of the wide portion.

The retaining member can have a central opening for allowing the inside portion to pass therethrough.

The retaining member can have a torus shape.

The head member can further be configured with a frontal portion with a rounded profile. The rounded profile can be a sphere-like profile.

The dispatching member can have an annular shape and can be configured with a perimetric rim for sealingly circumferentially fixing to the sleeve end, a nozzle for allowing the internal portion to pass therethorugh, and an inlet for interfacing with a pumping mechanism configured for introducing the propelling fluid into the space.

The dispatching member can be configured with a nozzle disposed at its center.

The system and the device can comprise a pumping mechanism for introducing the propelling fluid into the space, thereby generating a positive pressure therein and exerting the force on the everting portion.

The eversion sleeve can be made of one of the following materials: silk, nylon, rubber, deformable plastic material.

The eversion sleeve can be made of a fluid-tight material.

The space can be sealed from the surrounding.

The interior of the internal portion can define an elongate lumen allowing electrically or mechanically communicating therethrough between an exterior of the device at the surrounding of the dispatching member and the head member and its surrounding. The elongate lumen can allow introducing therethrough objects (e.g., endoscopes, measuring instruments, sensors, working tools), cables (e.g., electric cables, Bowden cables, fibers), or tubes.

The head member can be mounted to an operational unit including one or more of the following: a video camera, a stills camera, an imaging system, sensing system, a treatment system, a working tool, and a communication system.

The head member and the operational unit can be integrated into a single unit.

The head member can be mounted to a steering mechanism having a body member connected to a front end of the head member. The steering mechanism is configured for directing the head member during its advancing an article along the path.

The steering mechanism can comprise at least one pair of wheels and at least one controlling mechanism configured for controlling the direction of said pair of wheels.

The controlling mechanism can include at least one Bowden cable extending along the elongate lumen and a tensioning mechanism mounted to the at least one Bowden cable for controlling the direction of said pair of wheels.

The steering mechanism can comprise two pairs of wheels disposed consecutively with respect to each other and with respect to the head member. The frontal pair of the two pairs of wheels can be controllable by the controlling mechanism.

The steering mechanism can allow the head member to perform sharp turns along the path at an angle of about 90° or more than 90°.

Extraction of the propelling fluid from the space can reduce the force on the everting portion, thereby allowing gradually pulling back a segment of the inside portion towards the dispatching member and advancing a respective segment of the outside portion towards the head member, thereby drawing the head member backwardly along the path.

The system and the device can further comprise a reel on which the internal portion is wound around, for feeding the eversion sleeve via the dispatching member during supply of the propelling fluid into the space.

According to a further aspect of the presently disclosed subject matter, there is provided a method for assembling a system for advancing an article along a path, the system comprising: a head member having an internal portion, a dispatching member having a nozzle, and an eversion sleeve, the method comprising:

(i) introducing a part of said eversion sleeve via said nozzle;

(ii) everting the eversion sleeve inside out, thereby forming an outside portion having a sleeve end, an everting portion and an inside portion extending from the everting portion towards the dispatching member; and (iii) mounting said everting portion to said internal portion so as to retain the everting portion and facilitate it to slide with respect to the head member; and (iv) sealingly fixing said sleeve end to said dispatching member, thereby forming a space therebetween for receiving a propelling fluid for exerting force on the everting portion.

The method for assembling can further include a step of introducing said part of said eversion sleeve via a retaining member, which is performed between steps (i) and (ii), and a step of locating the retaining member at an internal surface of the everting portion for applying an outwardly pressing force thereon, which is performed between steps (iii) and (iv).

The step (iv) can further include a step of locating the retaining member within a wide portion of the head member.

According to a further aspect of the presently disclosed subject matter, there is provided a method for using a device for advancing an article along a path, comprising:

(i) providing the device, comprising: a head member; a dispatching member; an eversion sleeve configured with an outside portion having a sleeve end fixed to the dispatching member, an everting portion slidingly articulated to the head member and an inside portion extending from the everting portion towards the dispatching member; and a space formed between said inside portion and said outside portion;

said head member being configured with an internal portion for retaining the everting portion and facilitating the everting portion to slide with respect to the head member.

(ii) locating said device at a particular location at the path with the head member facing towards an advancement direction along the path; and (iii) introducing a propelling fluid into the space for exerting force on the everting portion, thereby gradually advancing a segment of the inside portion towards the head member causing it to slidingly displace with respect to the head member and gradually advancing a respective segment of the everting portion into the outside portion, thereby everting said eversion sleeve inside out and advancing the head member along the advancement direction.

The method can further comprise steps of: providing the device with a steering mechanism having a body member connected to a front end of the head member; and operating the steering mechanism for directing the advancement direction of the head member.

BRIEF DESCRIPTION OF THE DRAWINGS

In order to better understand the subject matter that is disclosed herein and to exemplify how it may be carried out in practice, embodiments will now be described, by way of non-limiting examples only, with reference to the accompanying drawings, in which.

DETAILED DESCRIPTION OF EMBODIMENTS

Attention is first directed to FIGS. 1A to 1D in which a system 1' (FIG. 1A) and a device 1 (FIGS. 1B to 1D) for advancing an article along a path are shown, in accordance with one example of the presently disclosed subject matter. The device 1 constitutes an assembled form of the system 1', and therefore, although explanations below are made with respect to the device 1, they are also relevant for the system 1'.

The device 1 comprises a head member 10, a retaining member 30, a dispatching member 50, an eversion sleeve 60, and a pumping mechanism in the form of a pump 90. The device 1 can optionally comprise an operational unit 100 which can be mounted to the head member 10 when needed.

Figure 1A:
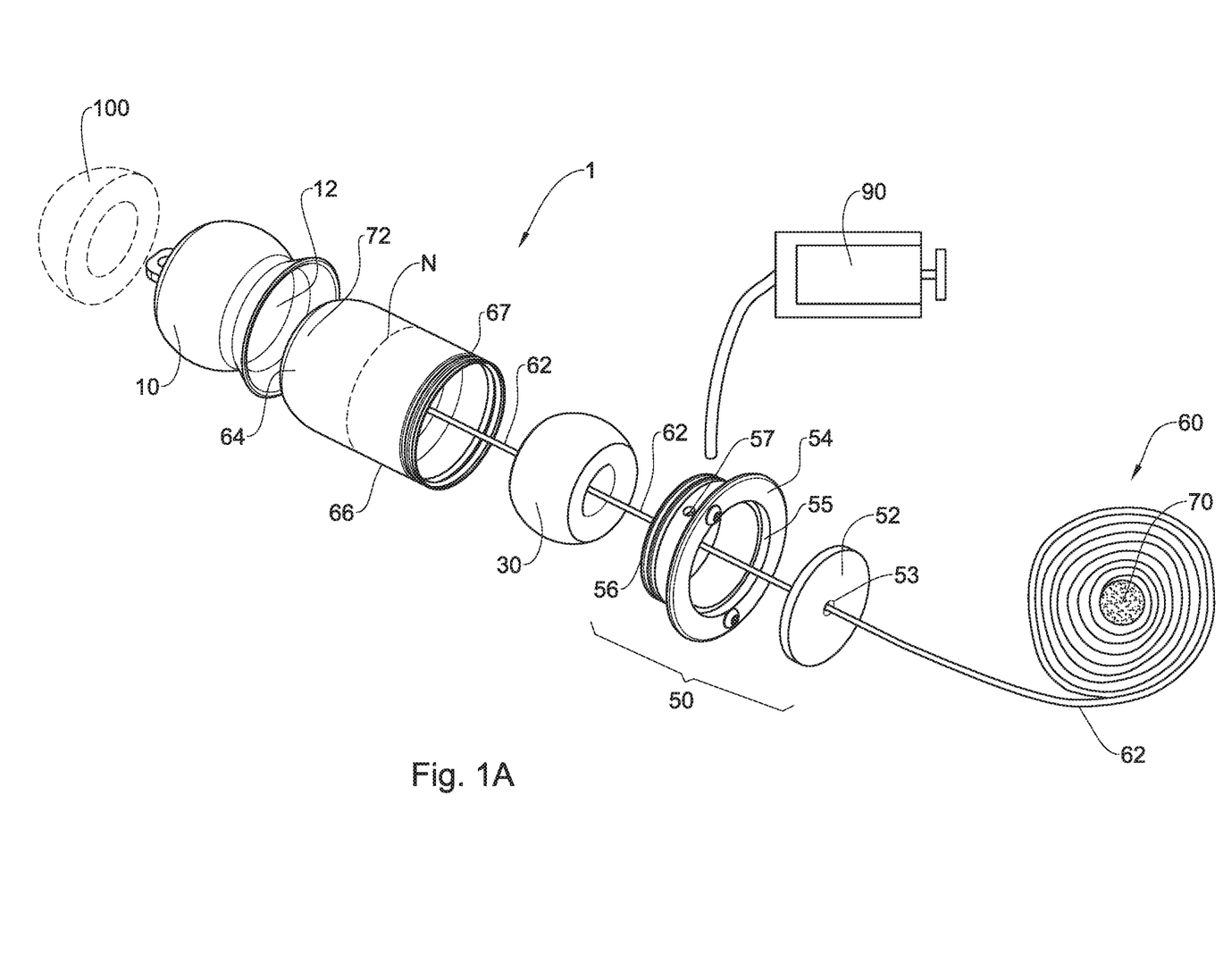
FIG. 1A is an exploded prospective view of a device according to one example of the presently disclosed subject matter, constituting a system for advancing an article along a path.
Figure 1B:
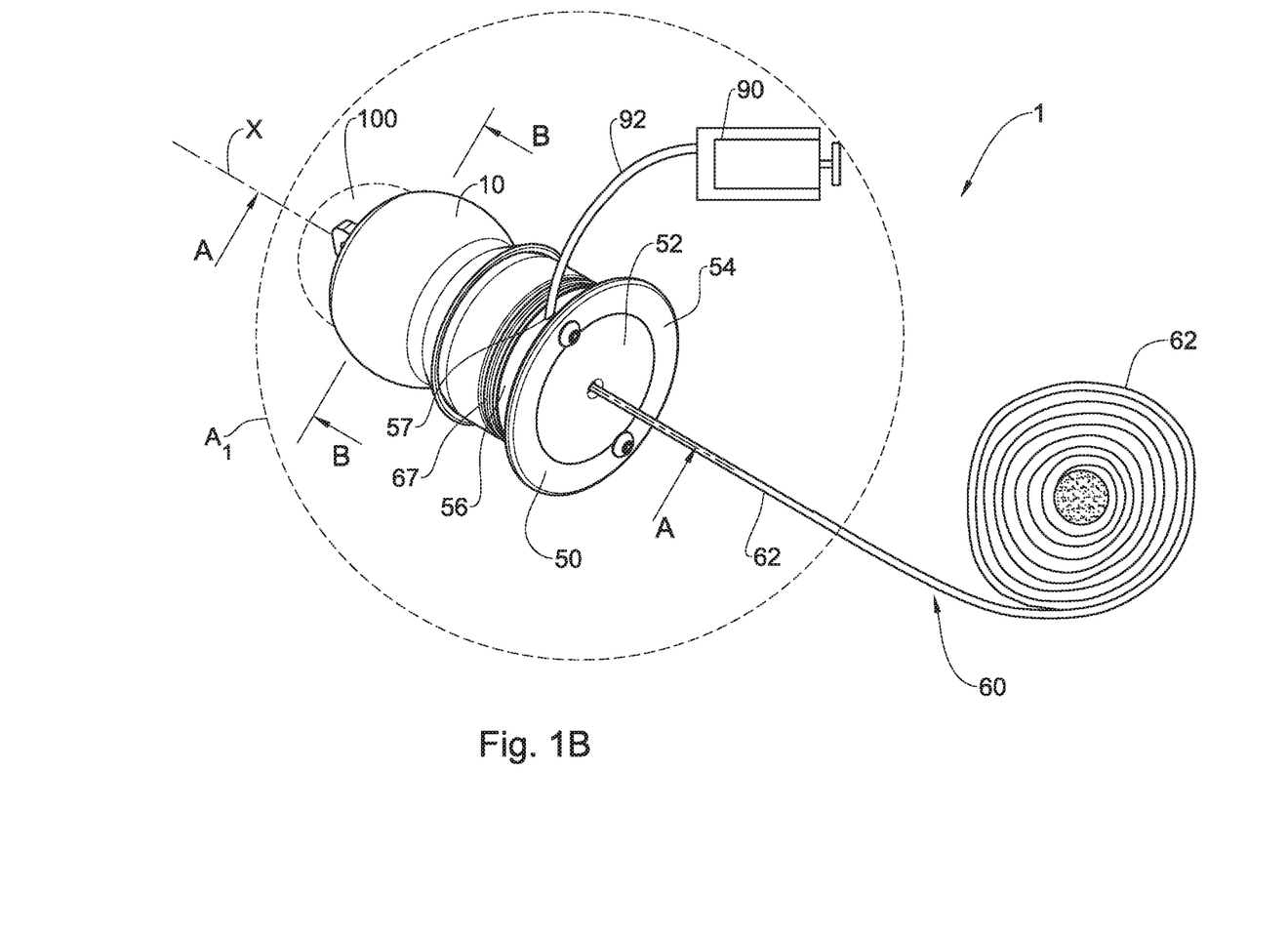
FIG. 1B is a rear perspective view of the device of FIG. 1A, in its initial state.
Figure 1C:
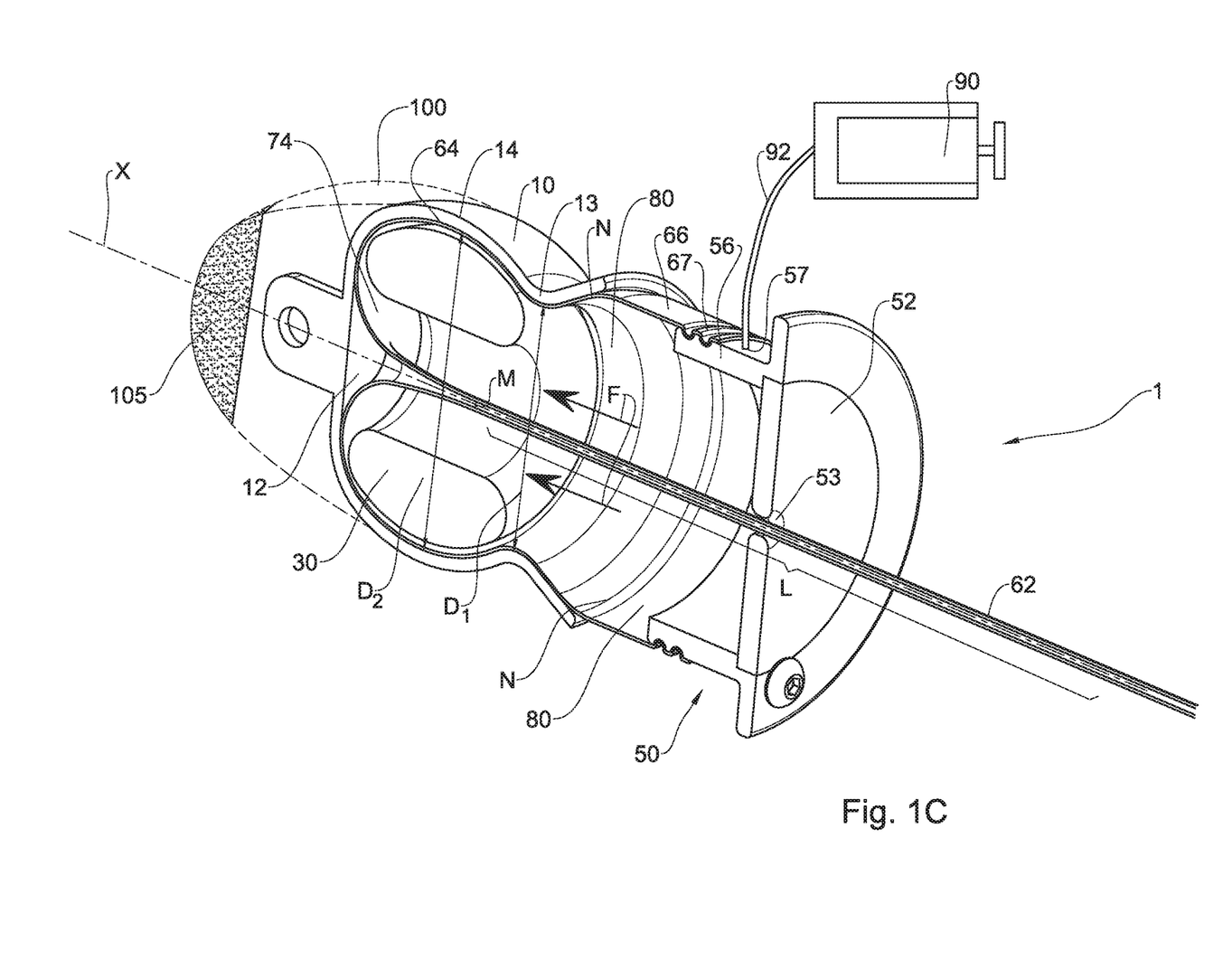
FIG. 1C is a cross-sectional view taken along line A-A of a portion A1 of the device of FIG. 1B.
Figure 1D:
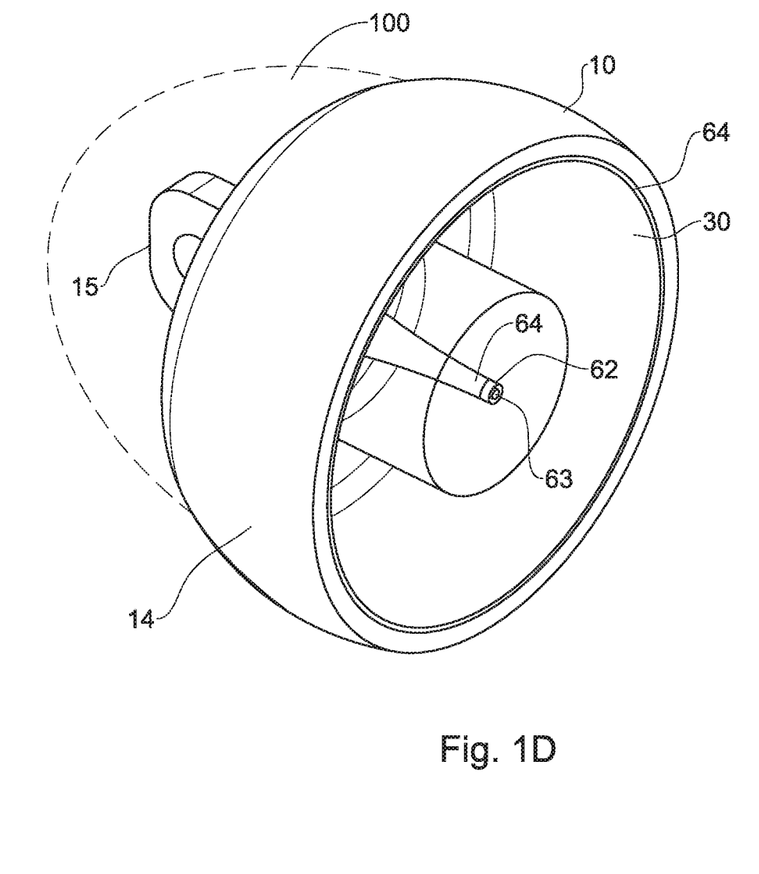
FIG. 1D is a cross-sectional view taken along line B-B of the device of FIG. 1B.

As shown in FIG. 1A, the eversion sleeve 60 is an elongate sleeve wound about a take-up reel 70. The eversion sleeve 60 is shown in FIG. 1A with its front end turned inside out, thereby forming three main portions: an inside portion 62, an everting portion 64 and an outside portion 66 which is turned at an angle of 180° with respect to the non-everted inside portion 62. As shown in FIG. 1C, the everting portion 64 is defined as a portion of the eversion sleeve 60 which extends between imaginary circles M and N of the sleeve. It should be indicated that the location of the everting portion 64, and respectively the length of the inside portion 62 and the outside portion 66 is dynamic, and depends on the extent of eversion of the eversion sleeve 60, as described below.

The eversion sleeve 60 is made of a fluid-tight material, for example, nylon. When being put under pressure, the eversion sleeve 60 is resilient and flexible, thereby allowing advancement of the head member 10 along a curved path, as explained below with reference to FIG. 3. Although the everting portion 64 of FIG. 1A is shown in its non-deformed state, when the device 1 is assembled, and particularly, when the head member 10 and the retaining member 30 are mounted to the everting portion, the shape of the everting portion is changed in accordance with the structure of the head member 10 and the retaining member 30 (as shown in FIG. 1C).

As explained below in a detailed manner, in operation of the device 1, introduction of a propelling fluid into the interior of the device 1 causes the eversion sleeve 60 to be continuously everted while increasing the length of the outside portion 66 and decreasing the length of the inside portion 62. This eversion is followed by sliding displacement of the head member 10 with respect to the eversion sleeve 60, which results in movement of the head member 10 along an elongation X-axis extending along the length of the device 1.

The dispatching member 50 includes an annular housing 54 with an opening 55 for sealingly receiving a closure 52 therein. The housing 54 is configured with a perimetric rim 56. As shown in FIGS. 1B and 1C, a sleeve end 67 of the outside portion 66 is sealingly fixed to the perimetric rim 56. The closure 52 has a nozzle 53 disposed at its center for allowing the inside portion 62 to pass therethorugh. The housing 54 further has an inlet 57 for interfacing with the pump 90 for fluidly communicating therebetween. The inside portion 62 is extending from the everting portion 64 towards the dispatching member 50, and from there to the take-up reel 70. The everting portion 64 is configured with an external surface 72 (shown in FIG. 1A) and an internal surface 74 (shown in FIG. 1C). The external surface 72 is engaging an internal portion 12 of the head member 10. The head member 10 is structured so as to retain the everting portion 64 in proximity thereto, while allowing and facilitating it to slide with respect to the internal portion 12. In particular, as shown in FIG. 1C, the internal portion 12 is configured with a narrow portion 13 having a first cross-sectional diameter D1 taken perpendicularly to its length along the X-axis. The narrow portion 13 is a circumferential groove formed in the head member 10. The internal portion 12 is further configured with a wide portion 14 having a second cross-sectional diameter D2 taken perpendicularly to its length along the X-axis. D2 is greater than D1. The narrow portion 13 is retaining the eversion sleeve by engaging the external surface 72 and preventing displacement of the head member 10 with respect to the everting portion 64 along the X-axis, while allowing the eversion sleeve 60 to slidingly displace with respect to the internal portion 12.

According to other examples, the head member may be configured with more than one narrow portion and/or with more than one wide portion. The narrow and the wide portions may be positioned at different combinations with respect to each other.

In addition to the structure of the head member 10, the retaining member 30 is also used for retaining the head member 10 to the eversion sleeve 60.

The retaining member 30 is a hollow resilient member having a torus shape, the exterior surface of which is mimicking the shape of surface of the wide portion 14.

The retaining of the head member 10 to the eversion sleeve 60 is performed by positioning the retaining member 30 at the wide portion 14 from the side of the internal surface 74, so that the everting portion 64 is disposed between the retaining member 30 and the head member 10. In this position, the retaining member 30 applies an outwardly pressing force on the internal surface 74, thereby retaining the everting portion 64 in proximity to the internal portion 12 while allowing the everting portion 64 to slidingly displace with respect to the internal portion 12.

As best seen in FIG. 1C, a fluid-tight sealable space 80 is formed within the device 1 between the inside portion 62 and the outside portion 66. The space 80 is in fluid communication with the pump 90 via a hose 92 which is connected to the inlet 57. The space 80 is sealed from the surrounding of the device 1 and is configured for receiving a propelling pressurized fluid in the form of air from the pump 90. The pump 90 can be manually or electrically operated.

Figure 2A:
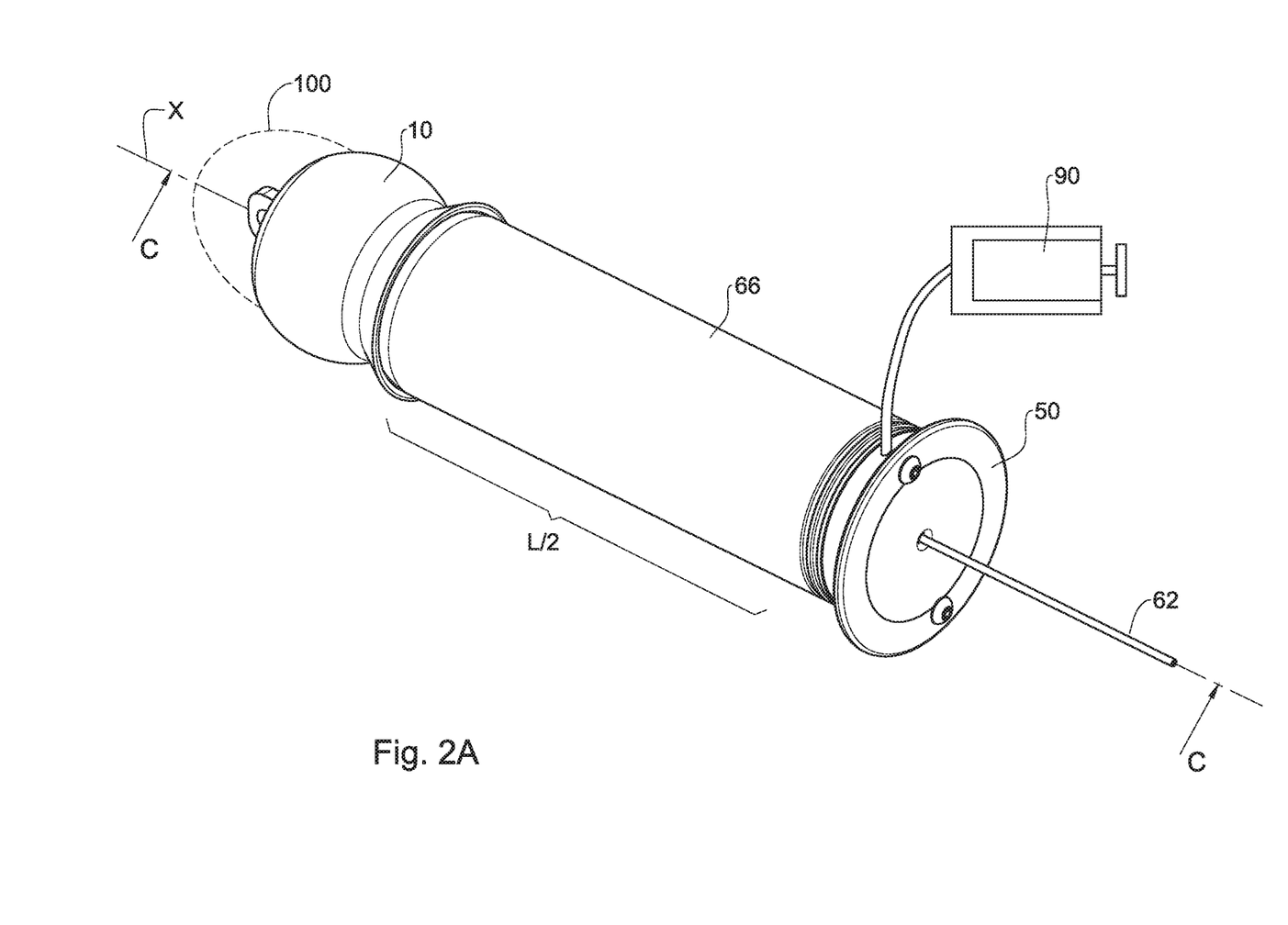
FIG. 2A is a rear perspective view of the device of FIG. 1B, in its elongated state.
Figure 2B:
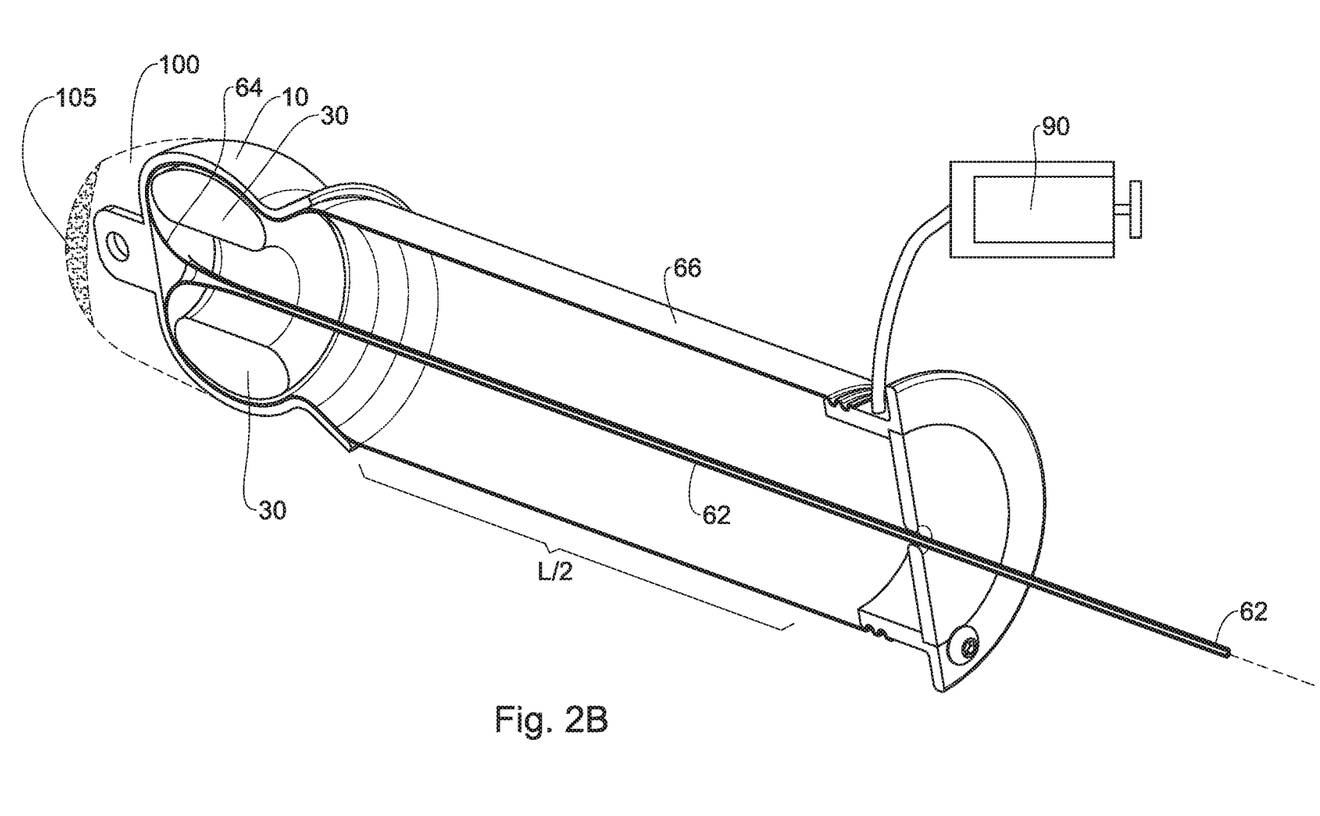
FIG. 2B is a cross-sectional view taken along line C-C of the device of FIG. 2A.

Reference is now made to FIGS. 2A and 2B in order to explain how introduction of air into the space 80 increases the length of the outside portion 66 while it remains stationary, thereby advancing the head member 10 along the X-axis by rolling the head member 10 with a sliding motion with respect to the eversion sleeve 60.

As a result of introduction of a predetermined amount of air into the space 80, a pressure gradient is generated within the space 80 with respect to the surrounding of the device 1. Due to a limited resilience of the eversion sleeve 60 in the radial direction, the pressure of the air within the space 80 generates a force F (shown in FIG. 1C) which is directed generally along the X-axis. The force F is exerted on the everting portion 64 straightly and via the retaining member 30. Exertion of the force F applies a pulling force on the inside portion 62 in the direction of the X-axis, gradually advancing a segment of the inside portion 62 towards the head member 10 with respective rotation of the take-up reel 70. This segment has a length L (shown in FIG. 1C). As a result of the pulling force applied thereon, the segment of the inside portion 62 slides between the head member 10 and the retaining member 30, gradually advancing a segment of the everting portion 64 into the outside portion 66. This results in increasing the length of the outside portion 66 by a length of L/2 and advancing the head member in the X-axis direction to a distance of L/2. In other words, the exertion of the force F causes eversion of a segment of the eversion sleeve 60 having the length L, which results in advancement of the head member 10 along a distance of L/2 (as shown in FIG. 2A). Therefore, during introduction of air into the space 80, the speed of advancement of the inside portion 62 is twice than the speed of advancement of the head member 10.

The head member 10 is made of a rigid material that preserves its shape also when the pressure of air within the space 80 drops, for example, when the head member 10 was advanced to a particular location along the path, and the pump 90 was disconnected from the device 1. This ability of the head member 10 to preserve its shape allows it to perform its designated function (e.g., measuring, sensing, optically inspecting, etc.) at any location along the path also when there is a pressure drop within the space 80.

The head member 10 is configured with a frontal portion having a rounded profile, and with an attachment member 15 disposed at its frontal edge. The attachment member 15 can be used for mounting different members to the head member 10 for different needs. According to the example of FIGS. 1A-1D and 2A-2B, the attachment member 15 can be optionally connected to the operational unit 100. The operational unit 100 includes a camera 105 at its frontal end (shown in FIGS. 1C and 2B). According to the example of FIGS. 4 and 5A-5B, the attachment member 15 can be used for mounting a steering mechanism thereto.

An interior of the internal portion 62 defines an elongate lumen 63 (shown in FIGS. 1C, 1D and 2B) allowing electrically or mechanically communicating therethrough between an exterior of the device at the surrounding of the dispatching member and the head member 10 and its surrounding. The lumen 63 can allow introducing therethrough into the location of the head member along the path different objects (e.g., endoscopes, measuring instruments, sensors, working tools), cables (e.g., electric cables, Bowden cables, fibers), or elongate elements. According to the present example, the lumen 63 can be used for passing therethorugh electric cables to the camera 105 for communicating with the camera 105 and providing power supply thereto.

Figure 3:
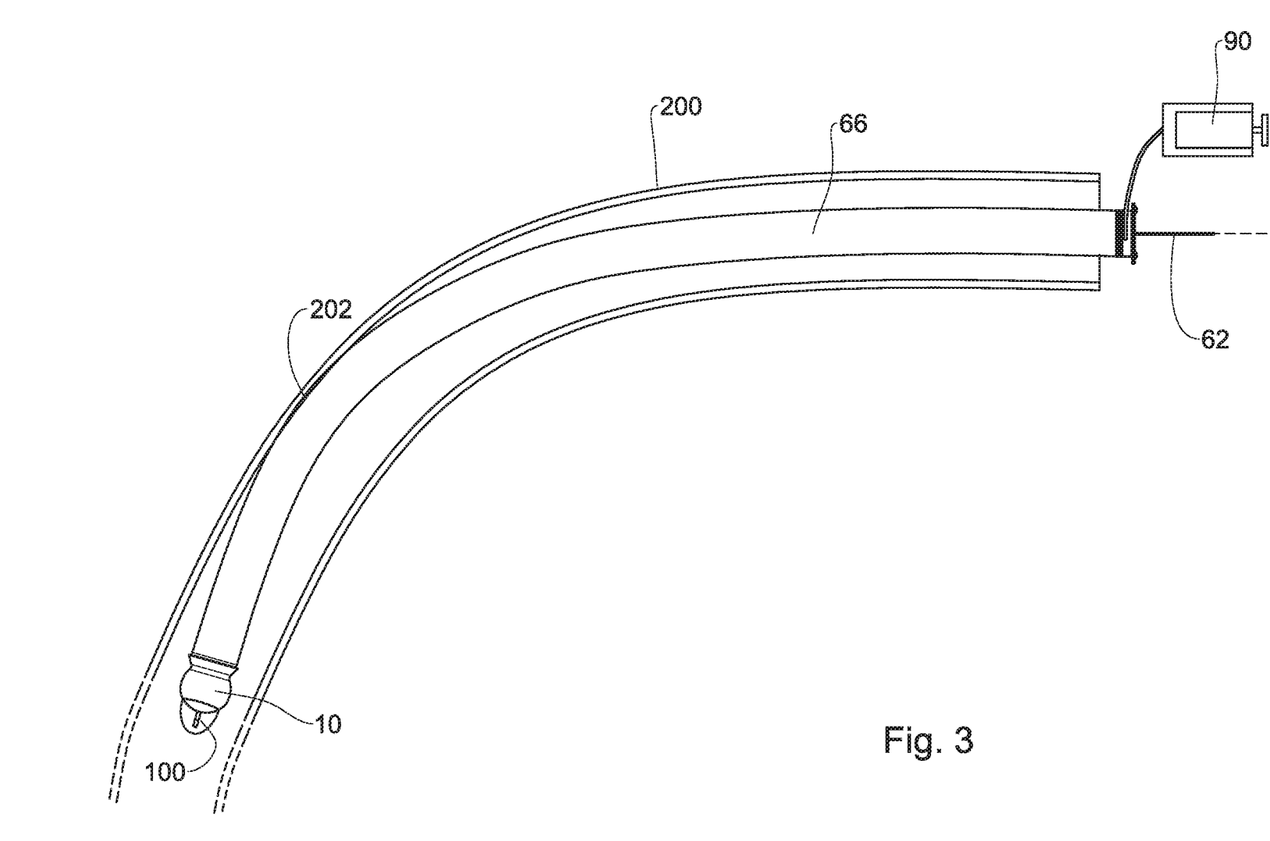
FIG. 3 is a top view of the device of FIG. 1B, in its elongated state along a path.

Reference is now made to FIG. 3 in which the device 1 is shown within a curved path 200. As mentioned above, the eversion sleeve 60 is made of a resilient and/or flexible material that allows advancing the outside portion 66 of the eversion sleeve 60 with the head member 10 mounted thereto along the curved structures. For example, when the head member 10 is advanced along the path 200, and reaches the wall of the path 200 at a turning point 202, further advancement of the head member 10 will cause the outside portion 66 to bend, thereby following the shape and the structure of the path 200.

The eversion process described above, which involves deployment of the eversion sleeve 60 by turning it inside out, allows advancing the head member 10 with a minimal friction along the path 200, since the outside portion 66 does not need to slide within the path 200 during the advancement of the head member 10. Therefore, the degree of the pressure of air that needs to be supplied into the space 80 for the advancement of the head member 10 along the path 200 is also reasonable.

It should be indicated that the head member 10 can also be advanced backwardly within path 200, for example, after finishing its intended operation. This can be done by reducing the pressure within the space 80, thereby allowing gradually pulling the inside portion 62 in the opposite direction, resulting in decrease of the length of the outside portion 62 and respective backward movement of the head member 10.

Although the eversion sleeve 60 has a finite length, its length can be manually or automatically increased by sealingly connecting thereto an additional eversion sleeve by known in the art techniques (e.g., heat welding). This can allow advancing the head member 10 along a path which is extremely long, even more than it was known to the operator prior to the introduction of the head member into the path.

Figure 4:
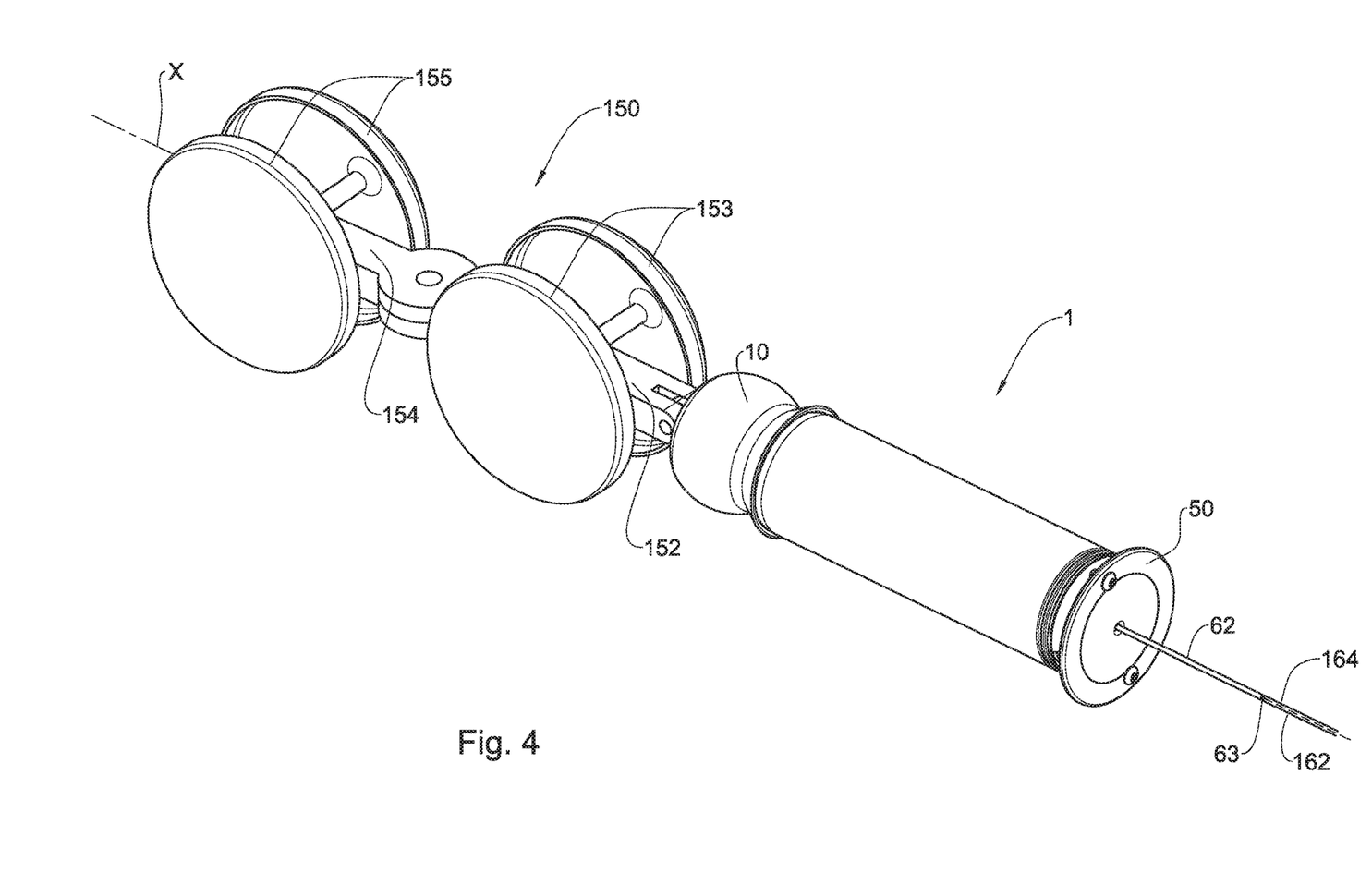
FIG. 4 is a rear perspective view of the device of FIG. 2A, configured with a steering mechanism mounted to its head member.
Figure 5A:
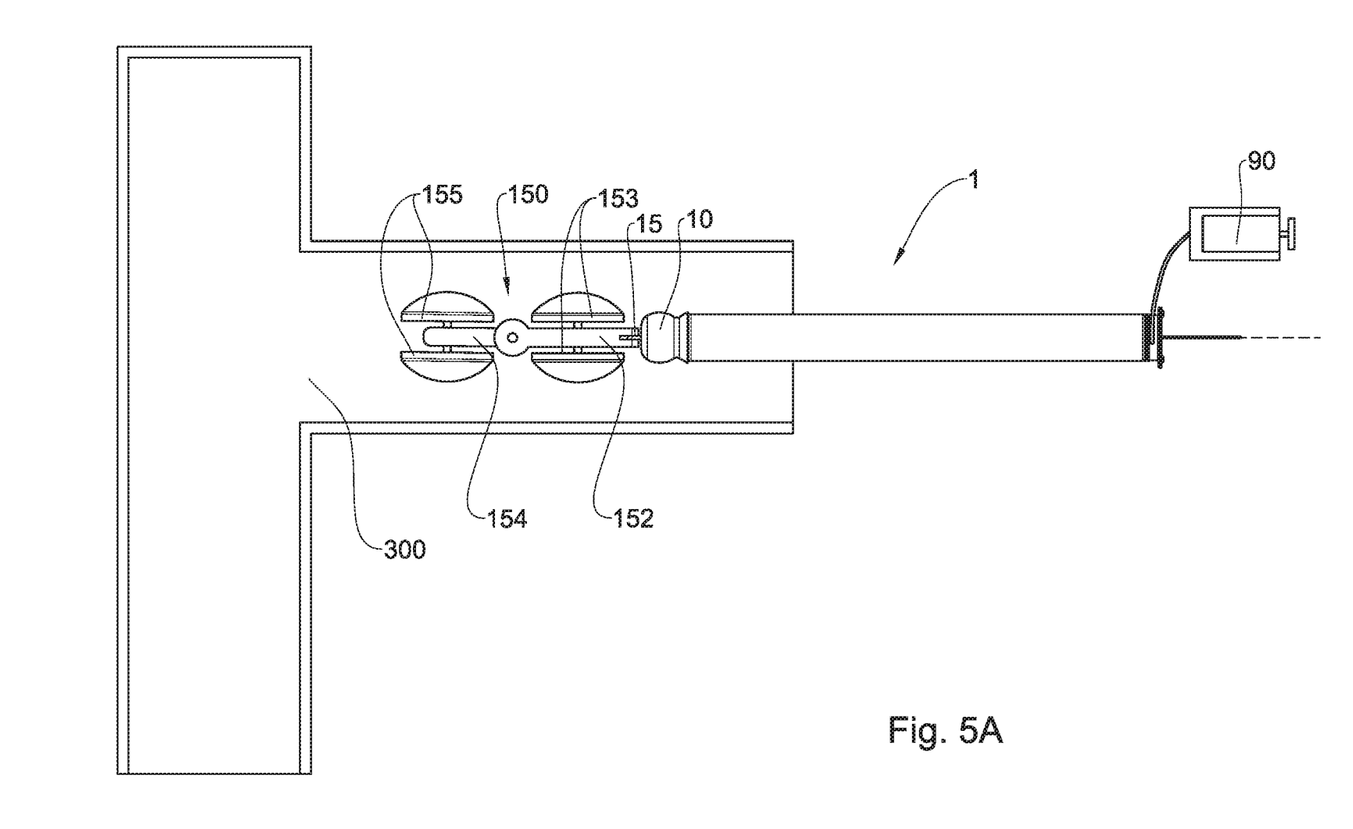
FIG. 5A is a top view of the device of FIG. 4, in its elongated state with particularly advancing an article along a path having a right-angled turn.
Figure 5B:
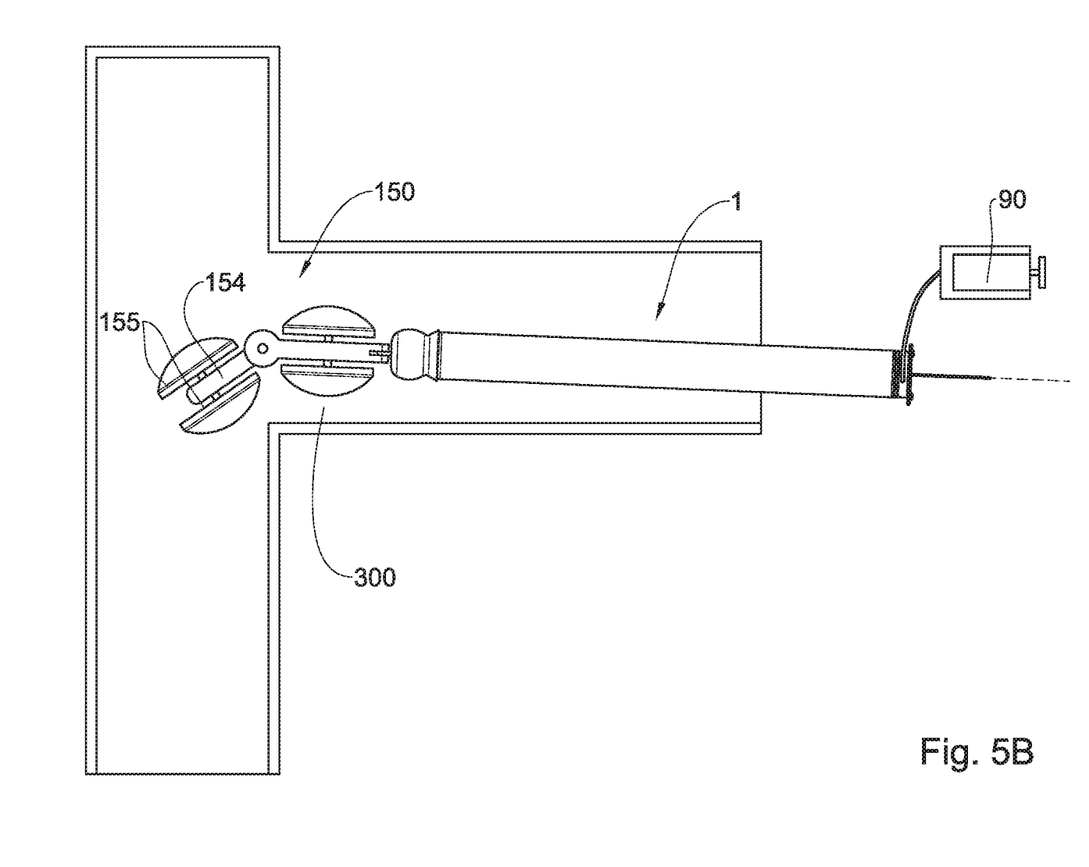
FIG. 5B is the device of FIG. 5A with further advancing an article along the path at the right-angled turn.

Reference is now made to FIGS. 4 and 5A-5B, in which the device 1 includes a steering mechanism 150 mounted to the head member 10. The steering mechanism 150 is configured for directing the head member 10 during its advancing an article along the path.

The steering mechanism 150 includes a first body member 152 and a second body member 154 pivotally connected therebetween. The first body member 152 is pivotally connected to the attachment member 15. The first body member 152 has a first pair of wheels 153 disposed at both its sides, and the second body member 154 has a second pair of wheels 155 disposed at both its sides. The wheels 153 and 155 are configured to be rotated by themselves upon advancement of the head member 10 along the path.

The steering mechanism 150 further includes a controlling mechanism (not shown) configured for controlling the direction of the pair of wheels. In particular, the controlling mechanism is configured for changing the direction of the first and the second body members 152 and 154 with respect to the X-axis and with respect to each other. The controlling mechanism is configured with two Bowden cables 162 and 164 (shown in FIG. 4), each connected to its respective body members 152 and 154. The Bowden cables extend within the lumen 63, along the entire length of the inside portion 62. The controlling mechanism further includes a tensioning mechanism mounted to the Bowden cables 162 and 164 for controlling the tension of these cables, and thereby changing the direction of the first and the second body members 152 and 154 with respect to the X-axis.

In FIGS. 5A-5B there is shown a path 300 having a sharp right-angled turn. As shown in FIG. 5B, in order to allow the head member 10 to turn left and not to be stuck at an injunction of the path, the second body member 154 is rotated by respective tensioning of the Bowden cable 164. This rotation allows the head member 10 to turn left and thereby continue its advancing an article along the path 300.

According to another example, when the structure of the path is unknown to the operator of the device 1, the steering mechanism can be used in conjunction with a video camera mounted to the head member or to the steering mechanism. The video camera can provide a real time picture of the region in front of the head member, and the steering mechanism can be used by the user for navigating the head member to a preferred direction.

The invention claimed is:

1. A system for advancing an article along a path, comprising:
   a head member;
   a dispatching member; and
   an eversion sleeve configured with an outside portion having a sleeve end configured to be fixed to the dispatching member, an everting portion configured for slidingly articulating to the head member and an inside portion configured to extend from the everting portion towards the dispatching member,
   said inside portion and said outside portion are configured to form a space therebetween for receiving a propelling fluid for exerting force on the everting portion, thereby advancing a segment of the inside portion towards the head member causing the segment to slidingly displace with respect to the head member and gradually advancing a segment of the everting portion into the outside portion, thereby everting said eversion sleeve inside out and advancing the head member along the path,
   wherein said head member is configured with an internal portion for retaining the everting portion and facilitating the everting portion to slide with respect to the head member.

2. The system according to claim 1, wherein the everting portion is configured with an external surface for engaging the internal portion of the head member, and an internal surface on which the force of the propelling fluid is to be exerted.

3. The system according to claim 2, wherein the internal portion of the head member is configured with at least one narrow portion having a first cross-sectional diameter D1 taken perpendicularly relative to a length of the head member and at least one wide portion having a second cross-sectional diameter D2 taken perpendicularly relative to the length of the head member, which D2 is greater than D1, said at least one narrow portion being configured to engage the external surface of the everting portion and prevent axial displacement of the head member with respect to the everting portion, while allowing the everting portion to slidingly displace with respect to the internal portion.

4. The system according to claim 3, wherein the narrow portion is formed as a circumferential groove in the head member.

5. The system according to claim 4, wherein the at least one narrow portion is configured to be disposed closer to the outside portion than the at least one wide portion.

6. The system according to claim 1, wherein the head member further comprises a retaining member configured for engaging the internal surface of the everting portion and applying an outwardly pressing force thereon, thereby retaining the everting portion in proximity to the internal portion while allowing the everting portion for slidingly displacing with respect to the internal portion.

7. The system according to claim 6, wherein the internal portion of the head member is configured with at least one narrow portion having a first cross-sectional diameter D1 taken perpendicularly relative to a length of the head member and at least one wide portion having a second cross-sectional diameter D2 taken perpendicularly relative to the length of the head member, which D2 is greater than D1, said at least one narrow portion being configured to engage the external surface of the everting portion and prevent axial displacement of the head member with respect to the everting portion, while allowing the everting portion to slidingly displace with respect to the internal portion, and wherein the retaining member has an exterior face having a shape which is mimicking a shape of the at least one wide portion.

8. The system according to claim 1, wherein the dispatching member has an annular shape and is configured with: a perimetric rim for sealingly circumferentially fixing to the sleeve end; a nozzle for allowing the internal portion to pass therethorugh; and an inlet for interfacing with a pumping mechanism configured for introducing the propelling fluid into the space.

9. The system according to claim 1, wherein an interior of the internal portion defines an elongate lumen allowing electrically or mechanically communicating therethrough between an exterior of a device defined by the dispatching member and the head member at a surrounding of the dispatching member and the head member.

10. The system according to claim 1, wherein the head member is configured to be mounted to a steering mechanism having a body member connected to a front end of the head member; said steering mechanism being configured for directing the head member during the head member advancing an article along the path.

11. The system according to claim 1, wherein extraction of the propelling fluid from the space is configured to reduce the force on the everting portion, thereby allowing gradually pulling back a segment of the inside portion towards the dispatching member and advancing a segment of the outside portion towards the head member, thereby drawing the head member backwardly along the path.

12. A device for advancing an article along a path, comprising:
- a head member;
- a dispatching member;
- an eversion sleeve configured with an outside portion having a sleeve end fixed to the dispatching member, an everting portion slidingly articulated to the head member and an inside portion extending from the everting portion towards the dispatching member; and
- a space formed between said inside portion and said outside portion for receiving a propelling fluid for exerting force on the everting portion, thereby gradually advancing a segment of the inside portion towards the head member causing the segment to slidingly displace with respect to the head member and gradually advancing a segment of the everting portion into the outside portion, thereby everting said eversion sleeve inside out and advancing the head member along the path, wherein said head member is configured with an internal portion for retaining the everting portion and facilitating the everting portion to slide with respect to the head member.

13. The device according to claim 12, wherein the everting portion is configured with an external surface engaging the internal portion of the head member, and an internal surface on which the force of the propelling fluid is to be exerted.

14. The device according to claim 13, wherein the internal portion of the head member is configured with at least one narrow portion having a first cross-sectional diameter D1 taken perpendicularly relative to a length of the head member and at least one wide portion having a second cross-sectional diameter D2 also taken perpendicularly relative to the length of the head member, when D2 is greater than D1, said at least one narrow portion being configured to engage the external surface of the everting portion and prevent axial displacement of the head member with respect to the everting portion, while allowing the everting portion to slidingly displace with respect to the internal portion.

15. The device according to claim 14, wherein the narrow portion is formed as a circumferential groove in the head member.

16. The device according to claim 14, wherein the narrow portion is disposed closer to the outside portion than the wide portion.

17. The device according to claim 12, wherein the head member further comprises a retaining member configured for engaging the internal surface of the everting portion and applying an outwardly pressing force thereon, thereby retaining the everting portion in proximity to the internal portion while allowing the everting portion for slidingly displacing with respect to the internal portion.

18. A method for assembling a system for advancing an article along a path, the system comprising: a head member having an internal portion, a dispatching member having a nozzle, and an eversion sleeve, the method comprising:
  (i) introducing a part of said eversion sleeve via said nozzle;
  (ii) everting the eversion sleeve inside out, thereby forming an outside portion having a sleeve end, an everting portion and an inside portion extending from the everting portion towards the dispatching member; and
  (iii) mounting said everting portion to said internal portion so as to retain the everting portion and facilitate the internal portion to slide with respect to the head member; and
  (iv) sealingly fixing said sleeve end to said dispatching member, thereby forming a space therebetween for receiving a propelling fluid for exerting force on the everting portion.

19. The method according to claim 18, further comprising steps of: introducing said part of said eversion sleeve via a retaining member, which is performed between said steps (i) and (ii); and locating the retaining member at an internal surface of the everting portion for applying an outwardly pressing force thereon, which is performed between said steps (iii) and (iv).

20. The method according to claim 19, further comprising a step of locating the retaining member within a wide portion of the head member.

* * * * *